(12) United States Patent
Ginn et al.

(10) Patent No.: US 6,461,364 B1
(45) Date of Patent: Oct. 8, 2002

(54) VASCULAR SHEATH WITH BIOABSORBABLE PUNCTURE SITE CLOSURE APPARATUS AND METHODS OF USE

(75) Inventors: Richard S. Ginn, San Jose; William N. Aldrich, Los Altos Hills; W. Martin Belef, San Jose, all of CA (US)

(73) Assignee: Integrated Vascular Systems, Inc., Sunnyvale, CA (US)

( * ) Notice: Subject to any disclaimer, the term of this patent is extended or adjusted under 35 U.S.C. 154(b) by 0 days.

(21) Appl. No.: 09/546,998

(22) Filed: Apr. 11, 2000

Related U.S. Application Data

(63) Continuation-in-part of application No. 09/478,179, filed on Jan. 5, 2000, now Pat. No. 6,197,042.

(51) Int. Cl.[7] .............................................. A61B 17/04
(52) U.S. Cl. ...................................... 606/142; 606/213
(58) Field of Search ................................ 606/143, 142, 606/151, 213, 219, 139

(56) References Cited

U.S. PATENT DOCUMENTS

| | | | |
|---|---|---|---|
| 3,586,002 A | 6/1971 | Wood | |
| 3,604,425 A | 9/1971 | Le Roy | 128/325 |
| 3,757,629 A | 9/1973 | Schneider | 85/49 |
| 3,805,337 A | 4/1974 | Branstetter | 24/27 |
| 4,192,315 A | 3/1980 | Hilzinger et al. | 128/346 |
| 4,217,902 A | 8/1980 | March | 128/325 |
| 4,396,139 A | 8/1983 | Hall et al. | 227/19 |
| 4,485,816 A | 12/1984 | Krumme | 128/334 |
| 4,505,274 A | 3/1985 | Speelman | |
| 4,586,503 A | 5/1986 | Kirsch et al. | 128/334 |
| 4,777,950 A | 10/1988 | Kees, Jr. | 128/325 |
| 4,860,746 A | 8/1989 | Yoon | 128/326 |
| 4,865,026 A | 9/1989 | Barrett | |
| 4,917,087 A | 4/1990 | Walsh et al. | 606/153 |
| 4,950,258 A | 8/1990 | Kawai et al. | |
| 5,007,921 A | 4/1991 | Brown | 606/221 |
| 5,026,390 A | 6/1991 | Brown | 606/221 |
| 5,053,008 A | 10/1991 | Bajaj | 604/104 |
| 5,061,274 A | 10/1991 | Kensey | 606/213 |
| 5,100,418 A | * 3/1992 | Yoon et al. | 606/139 |
| 5,108,420 A | 4/1992 | Marks | 606/213 |

(List continued on next page.)

FOREIGN PATENT DOCUMENTS

| | | | |
|---|---|---|---|
| WO | WO 97/20505 | 6/1997 | A61B 17/00 |
| WO | WO 98/24374 | 6/1998 | A61B 17/00 |

OTHER PUBLICATIONS

Amir Loshakove, et al., "Advanced Closure Device", PCT Publication No. WO 00/56227, Sep. 28, 2000.
Ari Derowe, et al., "Vascular Port Device", PCT Publication No. WO 99/62408, Dec. 9, 1999.
Amir Loshakove, et al., "Vascular Closure Device", PCT Publication No. WO 00/56223, Sep. 28, 2000.
Steven Tallarida, et al., "Vascular Suction Cannula, Dilator and Surgical Stapler", PCT Publication No. WO 0007640, Feb. 17, 2000.

*Primary Examiner*—Gary Jackson
(74) *Attorney, Agent, or Firm*—Lyon & Lyon LLP

(57) ABSTRACT

Apparatus and methods are provided for use in sealing a vascular puncture site. The invention comprises an introducer sheath with an integrated closure component. The closure component includes a fastener and an advanceable, deformable clip having a delivery configuration in which opposing sides do not contact one another, and a deployed configuration, in which the fastener causes opposing sides of the deformable clip to close towards one another. The clip is advanced along the sheath until it pierces opposing sides of a vessel wall at a puncture site. The clip is then deformed with the fastener to draw opposing sides of the puncture together, and the sheath is withdrawn to seal the wound. The clip and fastener preferably are bioabsorbable.

20 Claims, 4 Drawing Sheets

U.S. PATENT DOCUMENTS

| | | | |
|---|---|---|---|
| 5,156,609 A | 10/1992 | Nakao et al. | 606/142 |
| 5,176,648 A | 1/1993 | Holmes et al. | 604/164 |
| 5,192,302 A | 3/1993 | Kensey et al. | 606/213 |
| 5,222,974 A | 6/1993 | Kensey et al. | 606/213 |
| 5,304,184 A | 4/1994 | Hathaway et al. | 606/144 |
| 5,334,217 A | 8/1994 | Das | |
| 5,366,458 A | 11/1994 | Korthoff et al. | 606/151 |
| 5,478,353 A * | 12/1995 | Yoon | 606/213 |
| 5,478,354 A | 12/1995 | Tovey et al. | 606/219 |
| 5,527,322 A | 6/1996 | Klein et al. | 606/144 |
| 5,674,231 A | 10/1997 | Green et al. | 606/142 |
| 5,683,405 A | 11/1997 | Yacoubian et al. | 606/158 |
| 5,695,505 A | 12/1997 | Yoon | 606/157 |
| 5,782,844 A | 7/1998 | Yoon et al. | 606/139 |
| 5,782,861 A | 7/1998 | Cragg et al. | 606/216 |
| 5,810,846 A | 9/1998 | Virnich et al. | 606/142 |
| 5,810,851 A | 9/1998 | Yoon | 606/148 |
| 5,830,125 A | 11/1998 | Scribner et al. | 606/139 |
| 5,879,366 A | 3/1999 | Shaw et al. | |
| 5,910,155 A | 6/1999 | Ratcliff et al. | 606/213 |
| 5,984,934 A | 11/1999 | Ashby et al. | |
| 6,007,563 A | 12/1999 | Nash et al. | 606/213 |
| 6,036,720 A | 3/2000 | Abrams et al. | |
| 6,077,281 A | 6/2000 | Das | 606/151 |
| 6,077,291 A | 6/2000 | Das | 606/213 |
| 6,080,182 A | 6/2000 | Shaw et al. | 606/213 |
| 6,080,183 A | 6/2000 | Tsugita et al. | 606/213 |

\* cited by examiner

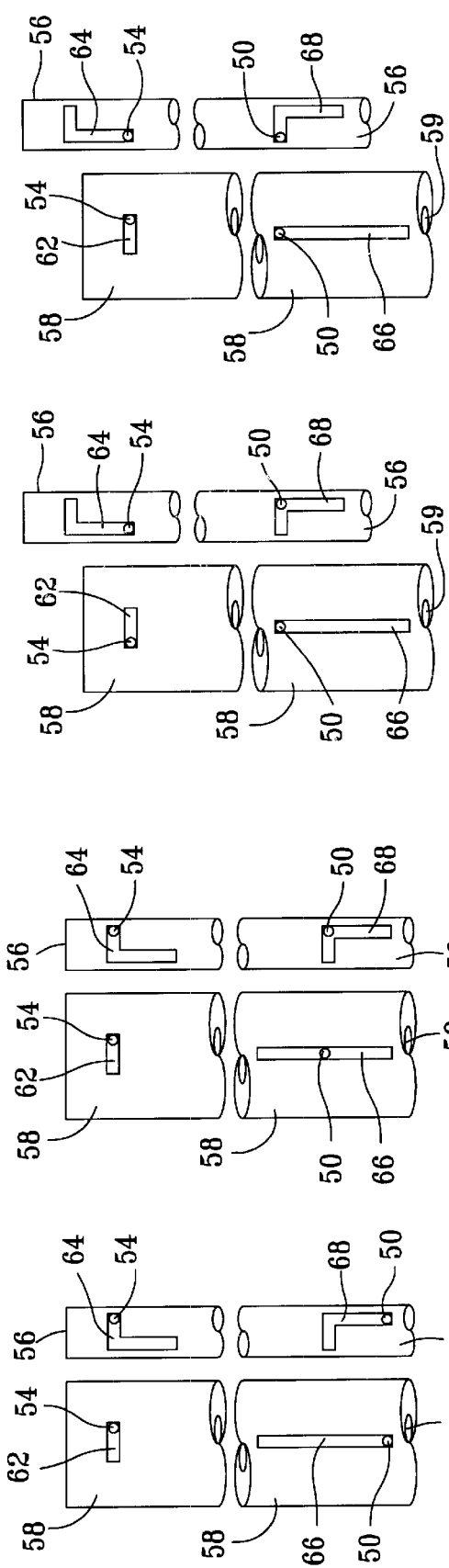
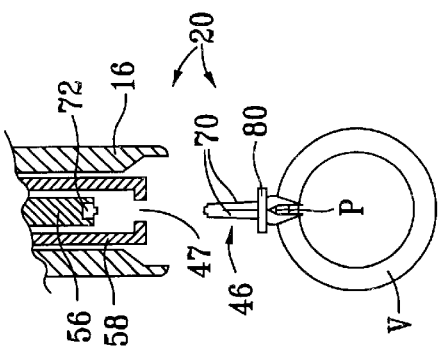
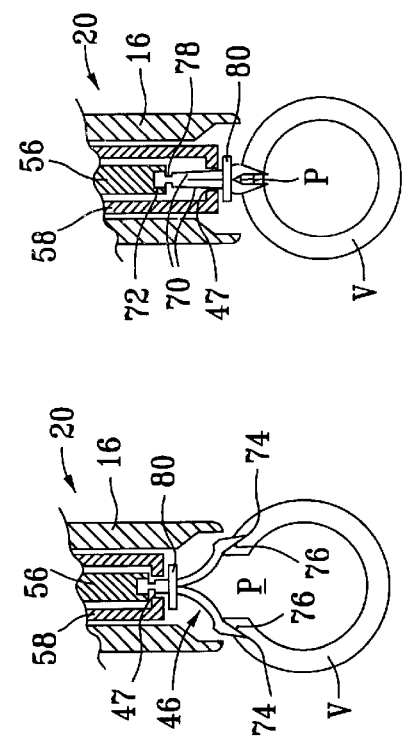
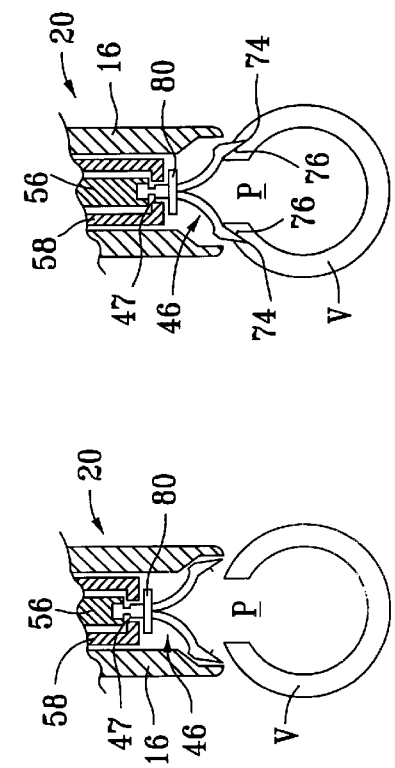

VASCULAR SHEATH WITH BIOABSORBABLE PUNCTURE SITE CLOSURE APPARATUS AND METHODS OF USE

REFERENCE TO RELATED APPLICATIONS

This application is a continuation-in-part of U.S. patent application Ser. No. 09/478,179 filed Jan. 5, 2000, now U.S. Pat. No. 6,197,042.

FIELD OF THE INVENTION

The present invention relates to apparatus and methods for sealing an iatrogenic puncture in a vessel formed in conjunction with a diagnostic or therapeutic treatment. More particularly, the present invention provides apparatus comprising an introducer sheath including a puncture site closure device comprising a bioabsorbable clip.

BACKGROUND OF THE INVENTION

Catheterization and interventional procedures, such as angioplasty and stenting, generally are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure.

Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurse's time, is uncomfortable for the patient, and requires that the patient be immobilized in the operating room, cathlab, or holding area. Furthermore, a risk of hematoma exists from bleeding prior to hemostasis.

Various apparatus have been developed for percutaneously sealing a vascular puncture by occluding or suturing the puncture site. For example, U.S. Pat. Nos. 5,192,302 and 5,222,974 to Kensey et al. describe the use of a biodegradable plug delivered through the introducer sheath into the puncture site. When deployed, the plug seals the vessel and provides hemostasis. Such devices have been slow to gain acceptance in the medical community, however, due to difficulties encountered in positioning the plug within the vessel.

Another previously known technique comprises percutaneously suturing the puncture site with specialized apparatus. Such apparatus is described, for example, in U.S. Pat. No. 5,304,184 to Hathaway et al. While percutaneous suturing devices may be effective, a significant degree of skill may be required on the part of the practitioner. Because such devices are mechanically complex, they tend to be relatively expensive to manufacture.

Surgical staples and resilient clips for external skin wound closure are well known in the art, Examples include U.S. Pat. No. 5,026,390 to Brown and U.S. Pat. No. 5,683,405 to Yacoubian et al, which both describe resiliently deformable closure devices suitable for manual external application.

To reduce the cost and complexity of percutaneous puncture closure devices, such devices employing resilient or deformable clips have been developed. U.S. Pat. No. 5,478,354 to Tovey et al. describes the use of resilient clips in conjunction with a trocar to close abdominal puncture wounds. U.S. Pat. No. 5,810,846 to Virnich et al. describes a specialized apparatus for closing a vascular puncture site with a plastically deformable clip. The apparatus preferably is advanced over a guide wire through a cannula to the surface of the puncture site, where the staple-like clips are delivered to close the wound.

U.S. Pat. No. 5,782,861 to Cragg et al. describes specialized apparatus for closing a puncture site with a detachable clip. The apparatus comprises a hollow shaft having a distal end formed with one or more opposed pairs of resilient grasping prongs and that is advanced over a guide wire through a coaxial hollow tube to a position at the distal end of the tube just proximal of the puncture. The grasping prongs are extended beyond the distal end of the tube to grasp the vessel on opposing sides of the puncture. The shaft then is partially retracted, causing the prongs to contract within the tube, thereby sealing the puncture site.

The percutaneous puncture closure devices described in the foregoing patents have the drawback that a separate device must be deployed through the introducer sheath to close the puncture site, thus prolonging the procedure. Moreover, these devices generally require relatively complex apparatus and involve time consuming manipulation to achieve hemostasis.

In view of the foregoing, it would be desirable to provide apparatus and methods suitable for vascular puncture closure that overcome the disadvantages of previously known devices.

It also would be desirable to provide apparatus and methods that quickly and effectively achieve hemostasis.

It further would be desirable to provide vascular puncture closure apparatus and methods that do not require the introduction of additional apparatus at the completion of the catheterization procedure to achieve closure.

It still further would be desirable to provide apparatus and methods wherein all foreign materials left in a patient's body are bioabsorbable.

It would be desirable to provide vascular puncture closure apparatus and methods that are safe, lower cost, and easy to use.

SUMMARY OF THE INVENTION

In view of the foregoing, it is an object of the present invention to provide vascular puncture closure apparatus and methods that overcome disadvantages of previously known devices.

It also is an object of this invention to provide apparatus and methods suitable for vascular puncture closure that quickly and effectively achieve hemostasis.

It is a further object of the present invention to provide apparatus and methods for vascular puncture closure that do not require the introduction of additional apparatus at the completion of the catheterization procedure to achieve closure.

It is still further an object of the present invention to provide apparatus and methods wherein all foreign materials left in a patient's body are bioabsorbable.

It is yet another object of the present invention to provide vascular puncture closure apparatus and methods that are safe, lower cost, and easy to use.

These and other objects of the present invention are accomplished by providing a vascular introducer sheath having an integrated wound closure component. The closure component consists of a bioabsorbable and deformable clip with a bioabsorbable fastener and is disposed on and advanceable over the exterior of the introducer sheath in an expanded delivery configuration until opposite sides of the clip pierce a vessel on opposite sides of a puncture site. The clip is then mechanically deformed with the fastener into a deployed configuration, thereby drawing opposite sides of the puncture together and closing the wound. Means also are provided for confirming when the bioabsorbable clip has engaged the vessel wall to indicate to the surgeon that the clip may be deployed and the introducer sheath may be withdrawn.

In a preferred embodiment, the bioabsorbable clip resembles an inverted "Y" with pointed ends that puncture the vessel to be closed. The fastener comprises a bioabsorbable locking collar that may be advanced down the length of the clip to bring the pointed ends together.

In a second embodiment, the bioabsorbable clip comprises a hoop with pointed legs extending therefrom. The hoop has two points of reduced thickness spaced 180 degrees apart on the circumference of the hoop. The fastener comprises a bioabsorbable conical wedge that is pushed down into the hoop to force opposing sides of the hoop towards one another and bring the pointed legs together.

Advantageously, the wound closure component of the present invention is inexpensively integrated into a standard-size introducer sheath, thereby eliminating the need for a separate closure device at the conclusion of a catheterization procedure. The present invention provides quick, safe, effective, and easy-to-use apparatus for achieving vascular closure that overcome drawbacks of previously known devices. Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 5A–5B through 8A–8B are side-sectional views of the closure component of FIG. 2A in use at a vascular puncture site, with corresponding side views of the proximal and distal slots of FIGS. 2B and 2C, illustrating a method of sealing the puncture site with the present invention.

DETAILED DESCRIPTION OF THE INVENTION

The integrated vascular introducer sheath with closure component of the present invention overcomes disadvantages associated with previously known methods and apparatus for sealing a vascular puncture by providing a quick, simple, safe, lower cost, effective, and easy-to-use solution to wound closure. Apparatus constructed in accordance with the present invention provide vascular introduction and wound closure in a single device, eliminating the time and manipulation required to insert a separate closure device at the completion of a procedure.

Figure 1:
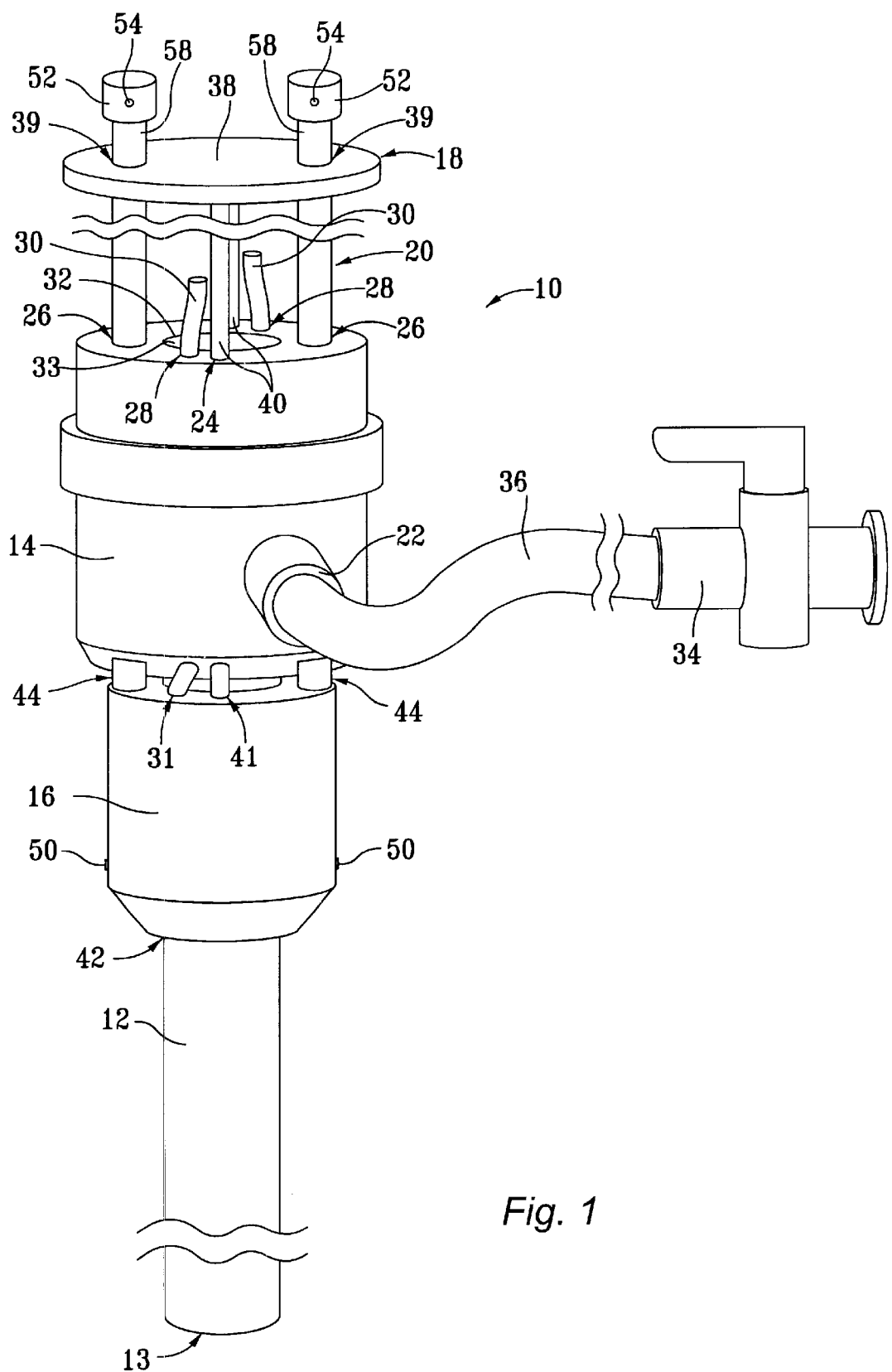
FIG. 1 is a side view of an integrated vascular device constructed in accordance with the present invention.

Referring to FIG. 1, a first embodiment of apparatus of the present invention is described. Vascular device 10 comprises introducer sheath 12 coupled to hub 14, clip housing 16 and clip actuator 18. A closure component 20, as described in detail hereinbelow, is disposed in clip housing 16.

Introducer sheath 12 comprises a material typically used for vascular introducer sheaths, such as polyethylene or nylon, and includes central lumen 13 through which other interventional devices may be introduced into the vasculature, for example, to perform a diagnostic or interventional procedure such as angiography, angioplasty, or stenting.

Hub 14 is mounted to the proximal end of introducer sheath 12 and includes side port 22, actuator lumens 24, closure lumens 26, backbleed lumens 28, backbleed tubes 30, and device port 32. Device port 32 communicates with central lumen 13 of introducer sheath 12, and has self-sealing elastomeric membrane 33 disposed across it. Self-sealing membrane 33, which may comprise, e.g., latex or a biocompatible synthetic rubber, permits interventional devices to be introduced through device port 32, while preventing blood loss through central lumen 13. Side port 22 of hub 14 is also in communication with central lumen 13, and is connected to hemostatic port 34 via biocompatible tubing 36.

Clip housing 16 includes two lumens, as described hereinbelow, that each hold a bioabsorbable, deformable clip. In accordance with the principles of the present invention, clip housing 16 is slidably disposed on the exterior of introducer sheath 12 and is movable from a stowed position, adjacent hub 14, to a distal clip deployment position, where the bioabsorbable clip is urged into engagement with tissue surrounding a vascular puncture. Clip housing 16 prevents the clips from snagging on tissue during advancement of clip housing 16.

Clip actuator 18 comprises plunger 38 and rods 40, which are configured to slidably pass through actuator lumens 24 of hub 14. Plunger 38 further includes openings 39. The distal ends of rods 40 are mounted in clip housing 16, so that movement of plunger 38 causes corresponding proximal or distal movement of clip housing 16. As described in detail hereinafter, when plunger 38 is moved to its proximal-most position, clip housing 16 is disposed adjacent to hub 14 and provides adequate clearance for interventional devices to be inserted through device port 32 and central lumen 13 into the patient's vasculature. When moved to its distal-most position, plunger 38 causes rods 40 to urge clip housing 16 distally.

Figure 2A:
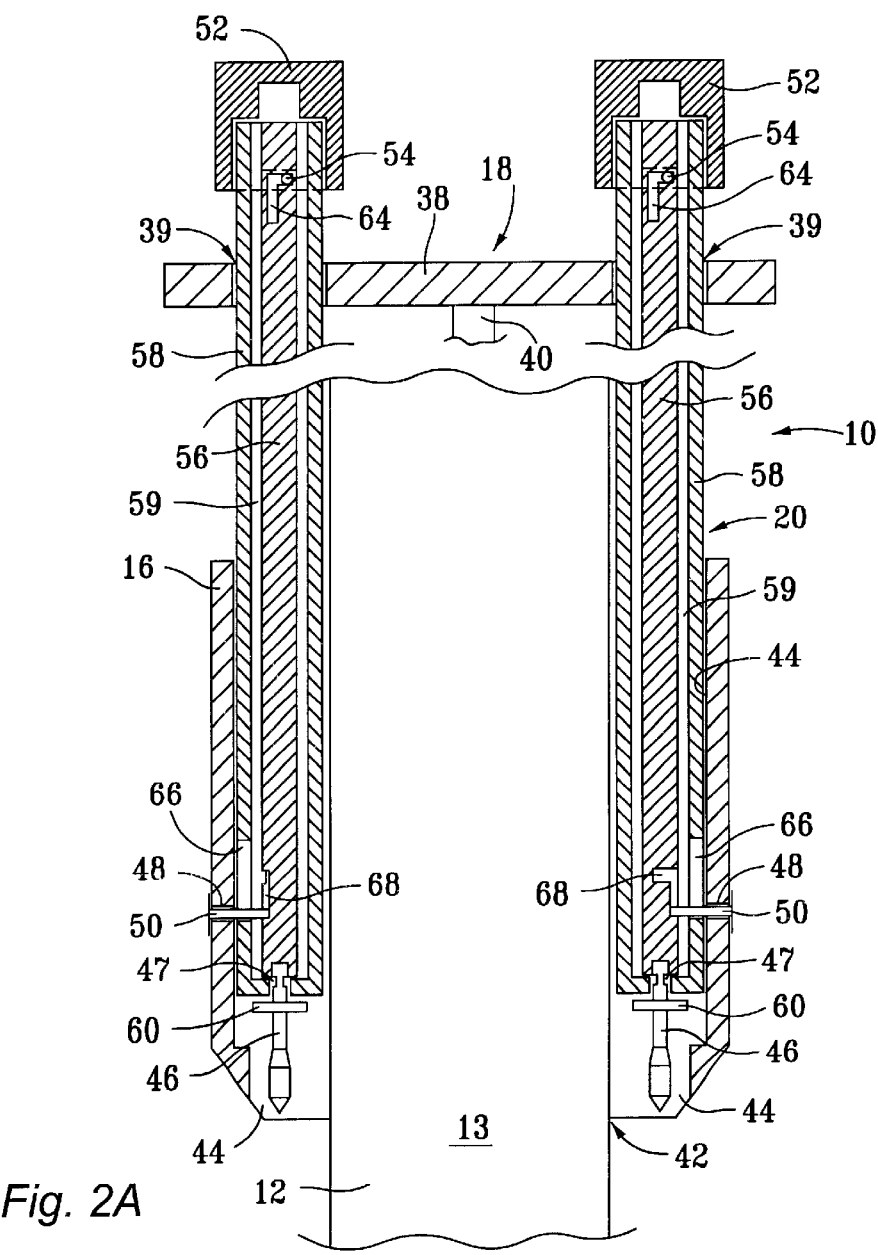
FIGS. 2A–2C are, respectively, a cross-sectional view of a closure component of the vascular device of FIG. 1, an exploded side view of proximal slots of the closure component, and an exploded side view of distal slots.

Referring now also to FIGS. 2, closure component 20 of vascular device 10 is described in greater detail. Clip housing 16 comprises lumen 42 that slidably receives introducer sheath 12, rod bores 41 (see FIG. 1) in which rods 40 are mounted, clip lumens 44 in which bioabsorbable clips 46 are housed and advanced to a puncture site, pin holes 48 for rigidly receiving distal pins 50, and backbleed indicator ports (not shown, out of the plane of the cross-section of FIG. 2A) that are coupled to backbleed tubes 30 via blood lumens 31.

Closure component 20 further comprises caps 52 with pin holes (not shown, out of the plane of the cross-section of FIG. 2A) configured to receive proximal pins 54, clip holders 56 attached to bioabsorbable clips 46, and locking collar drivers 58 configured to advance fasteners 60. Locking collar drivers 58 are slidably received within lumens 39 of plunger 38, closure lumens 26 of hub 14, and clip lumens 44 of clip housing 16. Drivers 58 further comprise lumens 59 and square clip bores 47, in which clip holders 56 and clips 46, respectively, are slidably received. Bores 47 are of square cross section.

Figure 2B:
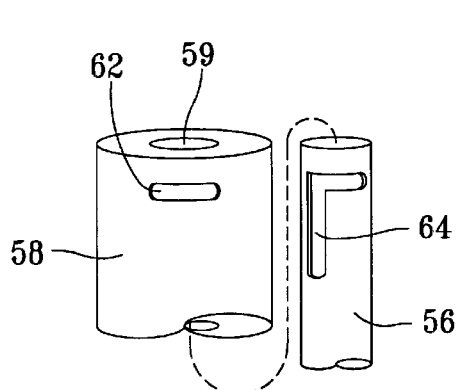
Figure 2C:
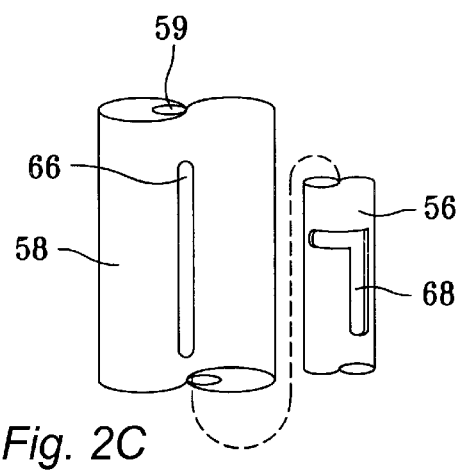

As illustrated in FIG. 2B, locking collar drivers 58 comprise proximal driver slots 62 that communicate with lumens 59, while clip holders 56 comprise proximal holder slots 64. Proximal pins 54, mounted in caps 52, pass through and are slidably received within slots 62 and 64. As seen in FIG. 2C, locking collar drivers 58 further comprise distal driver slots 66 that communicate with lumens 59, while clip holders 56 further comprise distal holder slots 68. Distal pins 50, mounted in clip housing 16, pass through and are slidably received within slots 66 and 68.

As discussed hereinabove, backbleed indicator ports (not shown) are coupled to backbleed tubes 30 via blood lumens 31 that extend through clip housing 16. Backbleed tubes 30 are slidably disposed through backbleed lumens 28 of hub 14. When the distal end of clip housing 16 is advanced distally against a vessel wall at a vascular puncture, blood enters the backbleed indicator ports and exits through tubes 30, providing visual confirmation to an operator that the distal end of clip housing 16 is positioned adjacent to the vessel wall. Backbleed tubes 30 thus enable the operator to determine when clip housing 16 has been sufficiently advanced to permit clip deployment, while reducing the risk that the clip is either deployed short of the puncture site or extended into the vessel.

In conjunction with clip deployment, a bioglue or tissue sealant may be delivered through hemostatic port 34, biocompatible tubing 36, side port 22 and central lumen 13 of introducer sheath 12 to the vascular puncture to further help seal the vessel after deployment of clips 46. Alternatively, the bioglue or tissue sealant may be delivered through device port 32 or through the backbleed path described above.

Figure 3A:
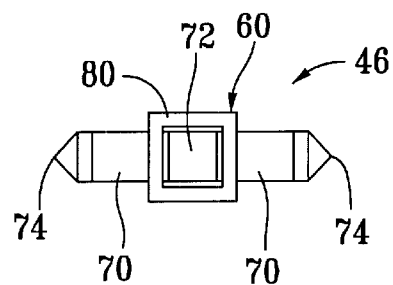
FIGS. 3A–3C are, respectively, views of a bioabsorbable clip and fastener of the present invention shown in top view in a delivery configuration, in side view in the delivery configuration, and in side view in a deployed configuration.
Figure 3B:
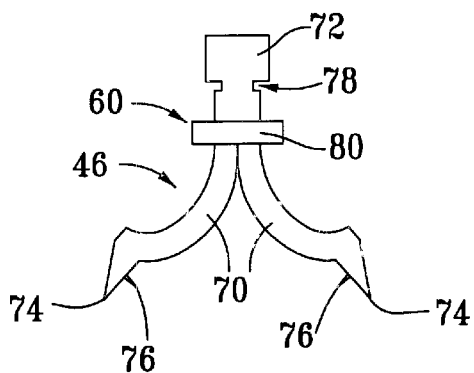
Figure 3C:
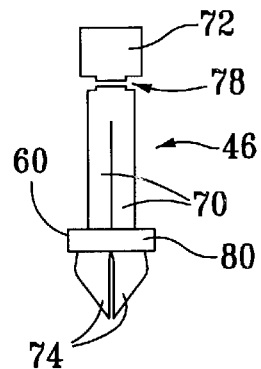

With reference now to FIGS. 3A–3C, bioabsorbable clip 46 and fastener 60 are described in greater detail. FIG. 3A shows clip 46 in the delivery configuration. Clip 46 comprises curved legs 70 and proximal end 72. Legs 70 distally terminate at spikes 74 with optional engagement means 76, and proximally terminate at narrowed region 78. Engagement means 76 may comprise, for example, barbs or hooks. As seen in FIG. 2A, proximal end 72 attaches to clip holder 56 by, for example, adhesive, and is slidably received by square clip bore 47 of locking collar driver 58. As with bore 47, clip 46 is of substantially square cross section.

Fastener 60 comprises bioabsorbable locking collar 80, which is slidably received on the exterior of clip 46. As seen in FIG. 3B, locking collar 80 may be distally advanced down the exterior of clip 46 to deform the clip to its deployed configuration, wherein curved legs 70 and spikes 74 are drawn together. Clip 46 may then be separated from clip holder 56 by rotating proximal end 72 with respect to legs 70, causing the clip to snap into two pieces at narrowed region 78, for the reasons described hereinafter. Clip 46 and locking collar 80 preferably are fabricated from bioabsorbable materials, such as polyglycolic acid.

Figure 4A:
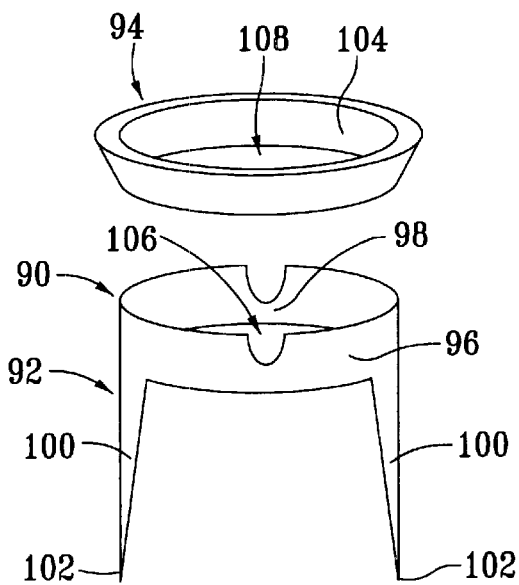
FIGS. 4A and 4B are isometric views of an alternative embodiment of the bioabsorbable surgical clip and fastener, constructed in accordance with the present invention and shown, respectively, in a delivery configuration and in a deployed configuration.
Figure 4B:
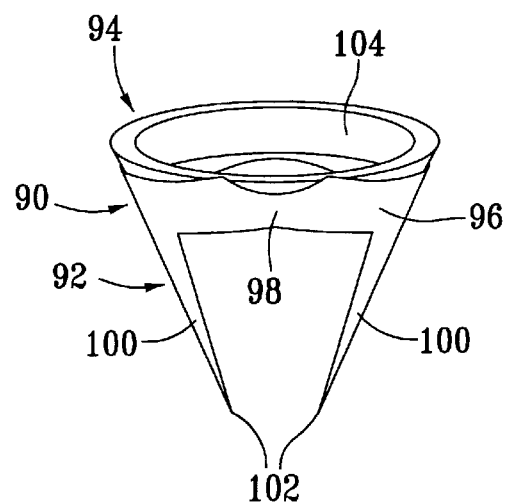

Referring to FIGS. 4, an alternative embodiment of the closure component of the present invention is described.

Closure component 90 comprises bioabsorbable clip 92 and fastener 94. Clip 92 comprises proximal hoop 96 with narrowed regions 98, and legs 100 terminating in spikes 102. Fastener 94 comprises bioabsorbable wedge 104. Wedge 104 has a diameter substantially equal to the diameter of hoop 96 at its distal end, the diameter tapering to a maximum diameter at the proximal end of wedge 104. Clip 92 therefore may be deformed from the delivery configuration of FIG. 4A to the deployed configuration of FIG. 4B, wherein legs 100 and spikes 102 are drawn together, by advancing wedge 104 into hoop 96 to deform clip 92 at narrowed regions 98. Lumen 106 extends through hoop 98 of clip 92, while lumen 108 extends through wedge 96. Clip 92 and wedge 96 therefore are configured for delivery over the exterior of an introducer sheath. The clip and wedge preferably are fabricated from bioabsorbable materials.

With reference to FIGS. 5A–5B through 8A–8B, in conjunction with FIGS. 1–3, methods of using vascular device 10 are described. Introducer sheath 12 is advanced through skin, fat, and muscle tissue into vessel V, through vascular puncture P, which is formed in accordance with well-known techniques. Vascular device 10 is used in the same manner as a standard introducer sheath, with instruments being advanced into the vessel via lumen 13. Specifically, with plunger 28 and rods 40 in the proximal-most, fully retracted position, an interventional procedure then is performed by introducing one or more interventional devices, e.g. angioplasty balloons, stent delivery systems, atherectomy devices, etc., through device port 32 and lumen 13 of introducer sheath 12 in accordance with well-known techniques. Side port 22 may be used to infuse fluids, e.g., contrast agents or medications, into the vessel through introducer sheath 12 during the interventional procedure.

Upon completion of the procedure, vascular device 10 advantageously may be used to close vascular puncture P. At this point, clip actuator 18, clip housing 16, and closure component 20 with clips 46, are disposed in the proximal-most position adjacent to hub 14.

Clip actuator 18 then is advanced by urging plunger 38 in the distal direction, thus causing rods 40 to slide through actuator lumens 24 of hub 14 and advance clip housing 16. Distal pins 50, mounted in housing 16, abut distal slots 66 and 68 of drivers 58 and holders 56, respectively. Thus, distal advancement of clip housing 16 also distally advances closure component 20. Continued distal advancement of plunger 38 causes the distal end of clip housing 16 to abut against the exterior of the vessel, so that the back bleed indicator ports (not shown) of clip housing 16 directly communicate with the puncture wound. The presence of pressure in the vessel higher than atmospheric pressure causes blood to pass through the indicator ports, through blood lumens 31, and exit through the proximal ends of tubes 30, thus confirming that clip housing 16 is positioned at the puncture site and should not be advanced further.

FIG. 5B illustrates closure component 20 via sectional views through clip housing 16 along planes parallel to introducer sheath 12. FIG. 5A shows the locations of proximal pins 54 within proximal slots 62 and 64, and the locations of distal pins 50 within distal slots 66 and 68, corresponding to the relative longitudinal positions of clip holders 56 and locking collar drivers 58 depicted in FIG. 5B. Pin locations are shown via side views of clip holders 56 and locking collar drivers 58 at the relevant locations.

As seen in FIGS. 5A and 5B, with clip housing 16 positioned at puncture site P, proximal pins 54, mounted in caps 52, are positioned at the extreme right of proximal driver slots 62 and of the circumferential portions of proximal holder slots 64. Distal pins 50 are located at the distal end of distal driver slots 66 and of the longitudinal portions of distal holder slots 68.

In FIGS. 6A and 6B, with clip housing 16 held immobile, force is applied to caps 52 to distally advance clips 46 with respect to housing 16. Specifically, proximal pins 54 abut and apply force against proximal slots 62 and 64, which advances drivers 58 and clip holders 56, as well as attached clips 46 and locking collars 80. Distal pins 50 move freely within distal slots 66 and the longitudinal portions of distal slots 68. Distal advancement of clips 46 continues until pins 50 abut against the proximal end of the longitudinal portions of distal holder slots 68 of clip holders 56. Drivers 58 likewise are restrained by their connection to clip holders 56 via proximal pins 54. The tissue-engaging members, spikes 74 and engagement means 76, of clips 46 contact and pierce the wall of vessel V on opposite sides of the puncture site P.

As seen in FIGS. 7A and 7B, once the spikes have pierced the vessel wall, locking collar drivers 58 are advanced distally while clip housing 16 and clip holders 56 remain stationary, thereby distally advancing locking collars 80 down the exteriors of clips 46 to draw legs 70 and spikes 74 together to close puncture P. Engagement means 76 serve to retain the clips within the vessel wall during healing.

To achieve this advancement of drivers 58 with respect to clip holders 56, caps 52 are rotated clockwise, as viewed from above, until proximal pins 54 abut against the extreme left of proximal slots 62 and 64, thereby aligning the pins with the longitudinal portions of proximal holder slots 64. Then, force is once again applied to caps 52 to advance drivers 58 and deform clips 46 to their deployed configurations. Specifically, proximal pins 54 abut and apply force to proximal driver slots 62, thereby distally advancing drivers 58. Pins 54 move freely within the longitudinal portions of proximal holder slots 64 until they abut against the distal ends of slots 64. Likewise, distal driver slots 66 move freely until distal pins 50 abut the proximal ends of slots 66. In FIG. 7A, when proximal pins 54 abut slots 64 and distal pins 50 abut slots 66, locking collars 80 have been driven down the exteriors of clips 46, thereby deforming the clips to draw legs 70 together and close the puncture site.

In FIGS. 8A and 8B, with clips 46 deformed to seal puncture P, clip holders 56 are detached from clips 46 by snapping the clips free at narrowed regions 78. At this point, or prior to detachment, a suitable biocompatible bioglue or tissue sealant optionally may be injected into the puncture tract, as discussed hereinabove, through device port 32 or side port 22, to aid in sealing vascular puncture P. Alternatively, the bioglue or tissue sealant may be delivered through the backbleed path described above. Vascular device 10 then is withdrawn from the vessel wall, completing the procedure.

Clips 46 are detached from clip holders 56 by rotating caps 52 counterclockwise, as viewed from above. Proximal pins 54 of caps 52 move freely within proximal driver slots 62, but abut against the distal end of the longitudinal portions of proximal holder slots 64 and cause clip holders 56 to rotate with respect to collar drivers 58. Distal pins 50 of clip housing 16 move freely within the circumferential portions of distal holder slots 68 during rotation of clip holders 56. Meanwhile, drivers 58 are restrained from rotation by distal pins 50, which abut against distal driver slots 66. Bioabsorbable clips 46 do not rotate because the square cross section of square clip bores 47 of drivers 58 matches the substantially square cross section of clips 46; thus, since drivers 58 are restrained from rotation, so are clips 46. Non-square cross sections for clips 46 and bores 47, capable of performing the restraining function, will be apparent to those of skill in the art and fall within the scope of the present invention.

Since clips 46 are restrained while clip holders 56 rotate, and since proximal ends 72 of clips 46 are attached to clip holders 56, counterclockwise rotation of caps 52 causes clips 46 to snap at their weakest points: narrowed regions 78. Vascular device 10 may then be removed from the patient to complete the procedure.

Although preferred illustrative embodiments of the present invention are described above, it will be evident to one skilled in the art that various changes and modifications may be made without departing from the invention. For example, with minor modifications, vascular device 10 may be configured to carry closure component 90 of FIGS. 4, or any of a variety of alternative bioabsorbable and deformable clips. Proximal pins 54 may be formed integrally with caps 52, and distal pins 50 may be formed integrally with clip housing 16. Any number of clips 46 may be used to close the vascular puncture. It is intended in the appended claims to cover all such changes and modifications that fall within the true spirit and scope of the invention.

What is claimed is:

1. Apparatus for sealing a puncture in a vessel wall comprising:
    an introducer sheath having proximal and distal regions and an exterior surface;
    a housing slidably disposed on the exterior surface of the introducer sheath, the housing including a lumen; and
    a closure component comprising a clip and a fastener,
    the clip having a delivery configuration, in which the clip is slidably accepted within the lumen, and a deployed configuration, wherein the fastener causes opposing sides of the clip to become directed inwards towards one another, to engage and close the puncture.

2. The apparatus of claim 1 further comprising an actuator for advancing the housing and closure component from the proximal end of the sheath to the vessel wall.

3. The apparatus of claim 2, wherein the actuator comprises at least one elongated member coupled to the housing.

4. The apparatus of claim 1, wherein the clip and fastener are bioabsorbable.

5. The apparatus of claim 1, wherein the clip comprises at least two elongated tissue-engaging members.

6. The apparatus of claim 5, wherein the at least two elongated tissue members are joined adjacent a proximal end, and the fastener comprises a locking collar slidably disposed over the proximal end.

7. The apparatus of claim 5 further comprising engagement means attached to the tissue-engaging members.

8. The apparatus of claim 6, wherein the closure component further comprises a clip holder attached to the proximal end of the clip and extending through the lumen and beyond the proximal region of the sheath.

9. The apparatus of claim 8, wherein the closure component further comprises a locking collar driver coaxially and slidably disposed over the clip holder, the locking collar driver configured to distally advance the locking collar to deform the clip to the deployed configuration.

10. The apparatus of claim 5, wherein the at least two elongated tissue-engaging members are coupled to a proximal hoop.

11. The apparatus of claim 10, wherein the fastener comprises a wedge.

12. The apparatus of claim 1 further comprising at least one backbleed indicator port coupled to a proximal end of the introducer sheath to indicate a position of the housing relative to the puncture.

13. The apparatus of claim 12, wherein a tissue sealant may be delivered through the indicator port to the vessel wall in a vicinity of the puncture.

14. The apparatus of claim 1 further comprising a side port for introducing fluids into the introducer sheath.

15. A method of sealing a puncture in a vessel wall, the method comprising:

providing apparatus comprising an introducer sheath having proximal and distal regions and a lumen extending therebetween, a housing slidably and coaxially disposed on the proximal region of the introducer sheath, and a closure component comprising a deformable clip and a fastener;

inserting the distal region of the introducer sheath through a patient's skin into a vessel via the puncture;

performing an interventional or diagnostic procedure by advancing a device through the lumen of the introducer sheath;

advancing the clip and housing through the skin until the clip pierces the vessel wall on opposing sides of the puncture;

deforming the clip with the fastener; and withdrawing the introducer sheath and housing to seal the puncture.

16. The method of claim 15 further comprising delivering a tissue sealant to the vessel wall in a vicinity of the puncture.

17. The method of claim 15, wherein the housing further comprises backbleed indicator ports coupled to the proximal region of the introducer sheath, the method further comprising advancing the clip and housing until blood from the puncture flows through the backbleed indicator ports to the proximal region of the introducer sheath.

18. The method of claim 15, wherein the apparatus further comprises a clip actuator coupled to the housing upon completion of the interventional or diagnostic procedure, and advancing the clip and housing through the skin comprises advancing the clip and housing through the skin with the clip actuator.

19. The method of claim 18, wherein the introducer further comprises a hub having a lumen and the clip actuator further comprises an elongated member, wherein coupling the clip actuator to the housing further comprises inserting the elongated member through the lumen of the hub.

20. The method of claim 15, wherein the closure component further comprises a clip holder attached to the clip and a locking collar driver slidably and coaxially disposed over the clip holder, and deforming the clip with the fastener comprises distally advancing the fastener by distally advancing the locking collar driver with respect to the clip holder.

* * * * *